United States Patent
Paul et al.

(10) Patent No.: US 9,918,788 B2
(45) Date of Patent: Mar. 20, 2018

(54) ELECTROGRAM-BASED ABLATION CONTROL

(71) Applicants: Saurav Paul, Minneapolis, MN (US); Charles Bryan Byrd, Oakdale, MN (US); James Holte, Minneapolis, MN (US); Mick Kuehn, Maple Grove, MN (US); Troy Tegg, Elk River, MN (US); Yitzhak Shai, Springfield, NJ (US); Robert Pacheco, Minneapolis, MN (US); Matt Pasvogel, Blaine, MN (US)

(72) Inventors: Saurav Paul, Minneapolis, MN (US); Charles Bryan Byrd, Oakdale, MN (US); James Holte, Minneapolis, MN (US); Mick Kuehn, Maple Grove, MN (US); Troy Tegg, Elk River, MN (US); Yitzhak Shai, Springfield, NJ (US); Robert Pacheco, Minneapolis, MN (US); Matt Pasvogel, Blaine, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 214 days.

(21) Appl. No.: 13/665,287

(22) Filed: Oct. 31, 2012

(65) Prior Publication Data
US 2014/0121659 A1    May 1, 2014

(51) Int. Cl.
| | |
|---|---|
| *A61B 18/12* | (2006.01) |
| *A61B 18/14* | (2006.01) |
| *A61B 34/20* | (2016.01) |
| *A61B 18/00* | (2006.01) |
| *A61B 34/30* | (2016.01) |

(52) U.S. Cl.
CPC ......... *A61B 18/1492* (2013.01); *A61B 34/20* (2016.02); *A61B 2018/00351* (2013.01); *A61B 2018/00648* (2013.01); *A61B 2018/00666* (2013.01); *A61B 2018/00839* (2013.01); *A61B 2034/2051* (2016.02); *A61B 2034/301* (2016.02)

(58) Field of Classification Search
CPC ..... A61B 18/12; A61B 18/1492; A61B 34/20; A61B 18/18
USPC ..................................... 606/41, 34
See application file for complete search history.

(56) References Cited

U.S. PATENT DOCUMENTS

| | | |
|---|---|---|
| 6,233,476 B1 | 3/2001 | Strommer et al. |
| 6,468,271 B1 | 10/2002 | Wentzel et al. |
| 6,498,944 B1 | 12/2002 | Ben-Haim et al. |

(Continued)

OTHER PUBLICATIONS

International Search Report and Written Opinion issued in International (PCT) Patent Application No. PCT/US2013/064222 (dated Jan. 7, 2014).

(Continued)

*Primary Examiner* — Carl H Layno
*Assistant Examiner* — Jon Eric C Morales
(74) *Attorney, Agent, or Firm* — Dykema Gossett PLLC (57) ABSTRACT

Methods, devices, and systems for predicting, diagnosing, and preventing adverse events during an ablation procedure are described. A method for providing ablation energy includes receiving a first signal based on biological activity of a tissue of a patient. The method further includes analyzing the first signal to yield a first data set, establishing a threshold parameter according to the first data set, and providing ablation energy for the ablation of a biological site.

20 Claims, 7 Drawing Sheets

(56) References Cited

U.S. PATENT DOCUMENTS

| | | |
|---|---|---|
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |
| 7,857,810 B2 | 12/2010 | Wang et al. |
| 2002/0123747 A1 | 9/2002 | Wenzel et al. |
| 2003/0204184 A1* | 10/2003 | Ferek-Patric .................. 606/41 |
| 2006/0247701 A1* | 11/2006 | Zacouto ........................... 607/9 |
| 2009/0163904 A1 | 6/2009 | Miller et al. |
| 2009/0247993 A1 | 10/2009 | Kirschenman et al. |
| 2010/0069921 A1* | 3/2010 | Miller ................ A61B 18/1233 606/130 |
| 2010/0168735 A1 | 7/2010 | Deno et al. |
| 2010/0168736 A1 | 7/2010 | Wang |
| 2010/0228247 A1 | 9/2010 | Paul et al. |
| 2011/0144657 A1 | 6/2011 | Fish et al. |
| 2012/0123400 A1* | 5/2012 | Francischelli ......... A61B 18/12 606/20 |

OTHER PUBLICATIONS

Bruce, et al., Discrepancies Between Catheter Tip and Tissue Temperature in Cooled-Tip Ablation, Circulation, Aug. 16, 2005, 954-960.

Haines, Biophysics of Ablation: Application to Technology, Journal of Cardiovascular Electrophysiology, vol. 15, No. 10, Oct. 2004, S2-S11.

Wittkampf, et al., RF Catheter Ablation: Lessons on Lesions, Pacing and Clinical Electrophysiology, vol. 29, Issue 11, Nov. 2006, 1285-1297.

* cited by examiner

ELECTROGRAM-BASED ABLATION CONTROL

BACKGROUND OF THE INVENTION a. Field of the Invention

The instant disclosure relates to medical ablation procedures, including detection and prevention of adverse events during cardiac ablation.

b. Background Art

During ablation procedures such as, for example, cardiac ablation procedures, it may be desirable to avoid or minimize adverse events that can result in damage to the tissue being ablated, such as charring of the tissue, localized coagulation, tamponade, effusion, steam pop, and tissue pop. Many of these adverse events can occur as a result of excessive energy delivery to an ablation site. Thus, it is generally desirable to monitor an ablation site for indications of adverse events during the provision of energy and reduce or interrupt the provision of energy if an adverse event is imminent.

Temperature and impedance are known inputs that can be evaluated for predicting, preventing, and diagnosing adverse events. For example, the local temperature at an ablation site (e.g., the temperature of an ablation electrode) can be monitored with a temperature sensor in or near the distal tip of an ablation catheter, such as described in U.S. Pat. No. 7,857,810, hereby incorporated by reference in its entirety as though fully set forth herein. In response to temperature measurements, the ablation generator can be controlled to increase, reduce, or cease the provision of ablation energy. Alternatively or additionally, irrigation fluid can be controlled responsive to a sensed temperature, such as described, for example, in U.S. Patent Application Publication No. 2010/0168736, hereby incorporated by reference in its entirety as though fully set forth herein. A high temperature may indicate a possible adverse event; however, accurately monitoring the temperature of several layers of tissue can be difficult.

Impedance also can be used for monitoring the condition of an ablation site for prediction and diagnosis of adverse events. For example, as discussed herein and described in U.S. Patent Application Publication No. 2011/0144657, which is hereby incorporated by reference in its entirety as though fully set forth herein, a complex impedance can be monitored for predicting endocardial barotrauma (sometimes referred to as "tissue pop"). Though impedance monitoring may provide a means for detecting adverse events, additional monitoring mechanisms and processes may be desirable to further increase the likelihood that an adverse event can be detected in advance and possibly prevented.

BRIEF SUMMARY OF THE INVENTION

The present disclosure relates to methods, devices, and systems for predicting, diagnosing, and preventing adverse events during an ablation procedure. The electrical activity of the heart can be monitored for signs of an oncoming adverse event, either alone or in conjunction with other information such as temperature or impedance. For example, an intracardiac electrogram can be monitored for an indication that an adverse event is imminent. In some cases, an increase in noise on an intracardiac electrogram caused, for example, by energy-induced blood microbubbles around an ablation site may generally precede an adverse event. In some embodiments, devices, systems, and methods are used to monitor an intracardiac electrogram for excessive noise during ablation. An adverse event or multiple events may be detected at their onset and minimized through appropriate preemptive action, such as appropriate or correlated control of ablation energy.

An embodiment of a device for controlling the provision of ablation energy may comprise a memory configured to store a threshold parameter and an electronic control unit (ECU). The ECU may be configured to receive a signal based on the biological activity of a patient and detected from inside the patient, analyze the signal to yield a data set, compare at least a portion of the data set to the threshold parameter to detect an ongoing adverse event, and modify the provision of ablation energy based, at least in part, on a comparison of the data set to the threshold parameter.

An embodiment of a system for performing an ablation procedure may comprise an ablation generator configured to provide ablation energy to a medical device including one or more electrodes and an electronic control unit (ECU). The ECU may be configured to receive a signal based on the biological activity of a patient and detected from inside the patient, analyze the signal to yield a data set, compare at least a portion of the data set to the threshold parameter to detect an ongoing adverse event, and provide a command for the ablation generator to modify the provision of ablation energy based, at least in part, on a comparison of the data set to the threshold parameter.

An embodiment of a method for providing ablation energy may comprise a number of steps, including a step of receiving a first signal based on the biological activity of a tissue of a patient, the biological activity detected from within the patient, analyzing the first signal to yield a first data set, and establishing a threshold parameter according to the first data set. Further steps may include providing ablation energy for the ablation of a biological site, receiving a second signal based on the biological activity of a tissue of a patient, the biological activity detected from within the patient, analyzing the second signal to yield a second data set, comparing at least a portion of the second data set to the threshold parameter to detect an ongoing adverse event, and modifying a parameter of provided ablation energy according to the comparison.

DETAILED DESCRIPTION OF THE INVENTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
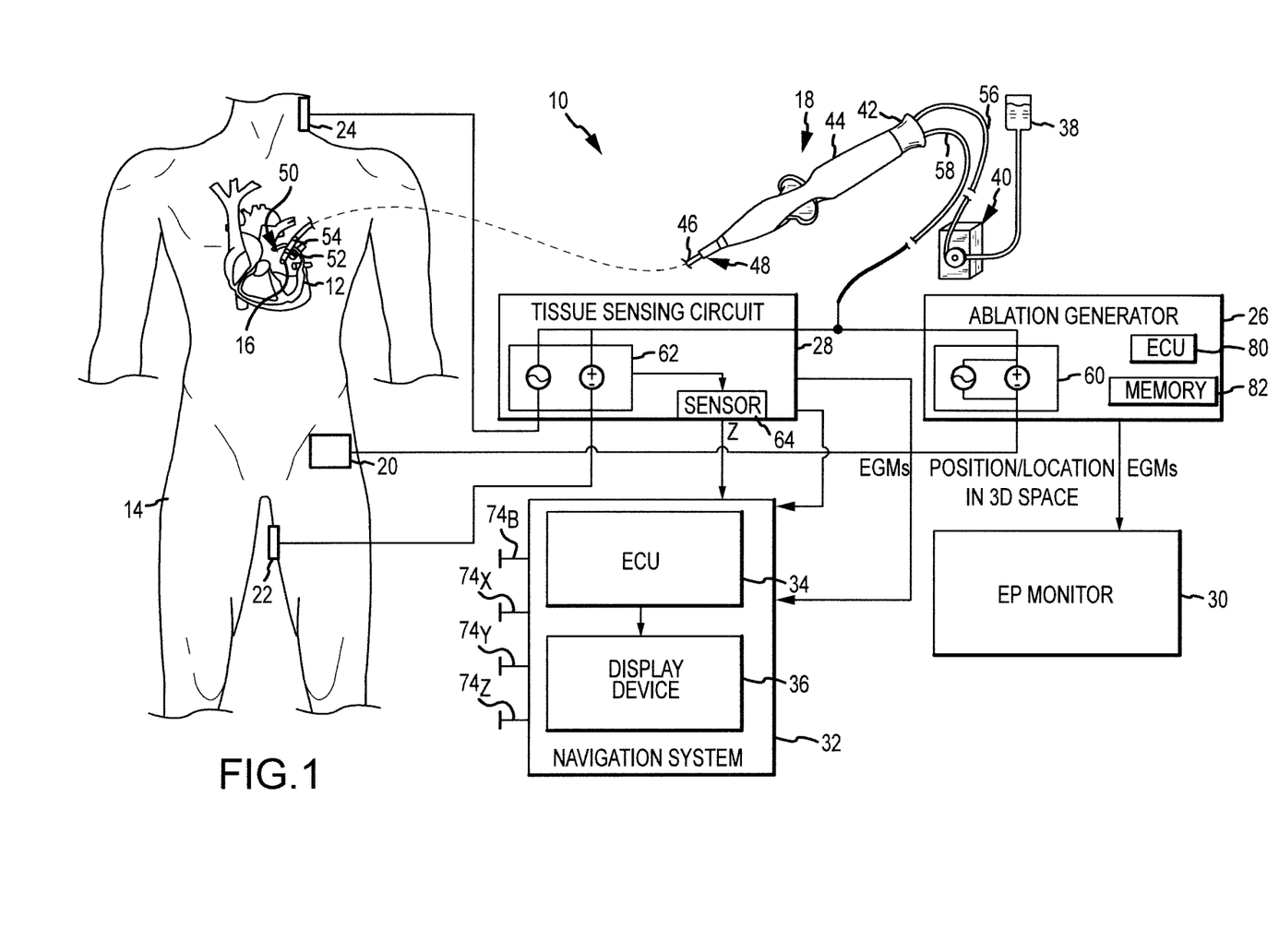
FIG. 1 is diagrammatic view of a system in accordance with an exemplary embodiment.

Referring now to the drawings wherein like reference numerals are used to identify identical components in the various views, FIG. 1 illustrates an exemplary embodiment of a system 10 configured, at least in part, for detecting the onset of an adverse event occurring in a tissue 12 of a body 14 during an ablation procedure. In an exemplary embodiment wherein the tissue 12 is cardiac tissue, the system 10 is configured to detect the onset of an adverse event occurring in the tissue 12 being ablated by radio frequency (RF) energy or power delivered from an electrode 16 disposed on the extreme distal tip of a catheter 18. For the sake of clarity and brevity, the description set forth below will be with respect to cardiac tissue. It should be understood, however, that the present disclosure may find application in connection with detecting the onset of adverse events occurring in other types of tissue during ablation procedures. Accordingly, the application of the present disclosure is not meant to be limited to that of cardiac tissue.

The system 10 supports functionality for detecting the onset of an adverse event based on a number of types of parameters. First, in some embodiments the system 10 may support the detection of an oncoming adverse event based on the electrical activity of a tissue of interest such as, for example, the heart. Second, in other embodiments the system 10 may also support the detection of an oncoming adverse event based on a complex impedance, such as described in greater detail in U.S. Patent Application Publication No. 2011/0144,657.

In addition to the electrode 16 and the catheter 18, embodiments of the system 10 may include patch electrodes 20, 22, 24, an ablation generator 26, a tissue sensing circuit 28, an electrophysiology (EP) monitor 30, and a system 32 for visualization, mapping, and navigation of internal body structures, which may include an electronic control unit 34 and a display device 36, among other components.

The catheter 18 can be provided for examination, diagnosis and treatment of internal body tissues such as the tissue 12. In accordance with one embodiment, the catheter 18 may comprise an ablation catheter and, more particularly, an irrigated radio-frequency (RF) ablation catheter. In an exemplary embodiment, the catheter 18 can be connected to a fluid source 38 having a biocompatible fluid, such as saline through a pump 40 for irrigation. The pump 40 may comprise, for example, a fixed or variable rate roller pump or variable volume syringe pump with a gravity feed supply from the fluid source 38, as shown. It should be noted, however, that the present disclosure is not meant to be limited to irrigated catheters, but rather it may find applicability with any number of electrode and ablation device combinations. In an exemplary embodiment, the catheter 18 can also be electrically connected to the ablation generator 26 for delivery of energy or power (e.g., RF energy or power). The catheter 18 may include a cable connector or interface 42, a handle 44, a shaft 46 having a proximal end 48 and a distal end 50, and one or more electrodes 16, 52, 54. The catheter 18 may also include other conventional components not illustrated herein, such as, for example, a temperature sensor, additional electrodes, and corresponding conductors or leads, or additional ablation elements (e.g., a high intensity focused ultrasound ablation element).

The connector 42 can provide mechanical, fluid and electrical connection(s) for cables 56, 58 extending from the pump 40 and the ablation generator 26. The connector 42 may be conventional in the art and disposed at or near the proximal end 48 of the catheter 18.

The handle 44 provides a location for a user (e.g., a clinician) to hold the catheter 18 and may further provide a means for steering or guiding the shaft 46 within the body 14. For example, the handle 44 may include means to change the length of a guidewire extending through the catheter 18 to the distal end 50 of the shaft 46 in order to steer the shaft 46 within the body. The handle 44 may also be conventional in the art and it will be understood that the construction of the handle 44 may vary. In an alternate exemplary embodiment to be described in greater detail below, the catheter 18 may be robotically or magnetically driven or controlled. Accordingly, rather than a clinician manipulating a handle to steer or guide the catheter 18, a robot or a magnetic-based system may be used to manipulate the catheter 18.

The shaft 46 may be an elongated, tubular, flexible member configured for movement within the body 14. The shaft 46 can support the electrodes 16, 52, 54, associated conductors. In some embodiments, the shaft 46 may further support additional components such as electronics used for signal processing or conditioning. The shaft 46 may be made from conventional materials such as polyurethane and defines one or more lumens configured to permit transport, delivery and/or removal of fluids (including irrigation fluids, cryogenic ablation fluids, and bodily fluids), medicines, and/or surgical tools or instruments. The shaft 46 may be introduced into a blood vessel or other structure within the body 14 through a conventional introducer. The shaft 46 may then be steered or guided through the body 14 to a desired location such as the tissue 12 with guidewires or other means known in the art.

The electrodes 16, 52, 54 can be provided for a variety of diagnostic and therapeutic purposes including, for example, electrophysiological studies, catheter identification and location, pacing, cardiac mapping, and ablation. In the illustrated embodiment, the catheter 18 includes an ablation tip electrode 16 at the distal end 50 of the shaft 46, and a pair of ring electrodes 52, 54. It should be understood, however, that the number, shape, orientation, and purpose of the electrodes 16, 52, 54 may vary.

In an embodiment, the electrodes 16, 52, 54 may be used to detect a signal representative of electrical activity of the tissue, which signal may be processed, displayed, stored, or otherwise represented as an electrogram. In an embodiment, the tissue of interest may be the heart or a chamber thereof. In an embodiment, the signal may be detected from within the tissue of interest. Accordingly, the electrogram may be an intracardiac electrogram. For the remainder of the disclosure, the electrogram will be described with reference to an intracardiac electrogram, though the disclosure is not so limited. For example, the electrogram may also be detected or captured by external electrodes, such as body surface patch electrodes. Furthermore, it should be understood that an "electrogram" may be used herein to refer to one or more signals that may be detected or captured by one or more electrodes, as well as to the representation of the one or more signals that may be displayed or stored.

The electrodes 16, 52, 54 may be used to capture, for example, a unipolar electrogram, a multi-polar electrogram (such as a bipolar electrogram), or both. In an embodiment, the electrogram can be captured while one or more of the electrodes 16, 52, 54 are in contact or close proximity with the tissue. A unipolar electrogram can be captured by a single electrode such as, for example and without limitation, the tip electrode 16. Such a unipolar electrogram may contain information about the local condition of the tissue (e.g., an ablation site within the heart), as well as information about other portions of the tissue (e.g., the broader electrical activity of the heart). A multi-polar electrogram can be captured by two or more electrodes such as, for example and without limitation, the tip electrode 16 and the second ring electrode 54. The signal detected by the ring electrode 54 (which may contain information about the broader electrical activity of the tissue) can effectively be subtracted from the signal detected by the tip electrode 16 (which may contain both local and broader information) to isolate the local electrical activity of the ablation site. Where a multi-polar electrogram is detected using three or more electrodes, the signals detected by all but one of the electrodes may be subtracted from the signal detected by the one other electrode, or the signals may be otherwise mathematically compared, averaged, or combined.

In some embodiments, an intracardiac electrogram, captured with one or more electrodes as described above or obtained from another source, may be monitored to detect an increase in noise, which may be indicative of the onset of an adverse event. If an electrogram indicates that an adverse event is imminent, then preemptive actions can be taken to lessen the likelihood of an adverse event, as discussed further herein. For example, ablation energy may be reduced, the ablation catheter may be retracted from the ablation site, and/or the flow of irrigation fluid may be altered. Other preemptive actions are also possible. In an embodiment, a remote catheter guidance system (RCGS) may automatically retract the ablation catheter from an ablation site based, at least in part, on a monitored electrogram. Several example preemptive actions are further described below.

The patch electrodes 20, 22, 24 can provide RF or navigational signal injection paths and/or can be used to sense electrical potentials. The electrodes 20, 22, 24 may also have additional purposes such as the generation of an electromechanical map. The electrodes 20, 22, 24 may be made from flexible, electrically conductive material and may be configured for affixation to the body 14 such that the electrodes 20, 22, 24 are in electrical contact with the patient's skin. The electrode 20 may function as an RF indifferent/dispersive return for the RF ablation signal. The electrodes 22, 24 may function as returns for the RF ablation signal source and/or an excitation signal generated by the tissue sensing circuit 28 as described in greater detail hereinbelow. In the illustrated embodiment, the electrodes 22, 24 are located on the medial aspect of the left leg and the dorsal aspect of the neck. The electrodes 22, 24 may alternatively be located on the front and back of the torso or in other conventional orientations.

The ablation generator 26 can generate, deliver, and control RF energy output by the ablation catheter 18, and the electrode 16, in particular. The generator 26 can be conventional in the art and may comprise a commercially available unit, such as that sold under the model number IBI-1500T-11 RF Cardiac Ablation Generator, available from Irvine Biomedical, Inc. The generator 26 can include an RF ablation signal source 60 configured to generate an ablation signal that is output across a pair of source connectors: a positive polarity connector SOURCE (+) which may connect to the tip electrode 16; and a negative polarity connector SOURCE (−) which may be electrically connected by conductors or lead wires to one of the patch electrodes 20, 22, 24 (see FIG. 2). It should be understood that the term connectors as used herein does not imply a particular type of physical interface mechanism, but is rather broadly contemplated to represent one or more electrical nodes. The source 60 can be configured to generate a signal at a predetermined frequency in accordance with one or more user specified parameters (e.g., power, time, etc.) and under the control of various feedback sensing and control circuitry, such as known in the art. The source 60 may generate a signal, for example, with a frequency of about 450 kHz or greater. The generator 26 may also monitor various input parameters associated with the ablation procedure including impedance, the temperature at the tip of the catheter, ablation energy, and/or the position of the catheter. During an ablation procedure, these input parameters can be provided as feedback to the clinician. The impedance measurement output by a typical generator 26 may reflect the magnitude of impedance not only at the tissue 12, but the entire impedance between the tip electrode 16 and the corresponding patch electrode 20 on the body surface. In an exemplary embodiment, the ablation generator 26 may generate a higher frequency current for the purposes of RF ablation, and a second, lower frequency current for the purpose of measuring impedance.

In an embodiment, the ablation generator 26 may also include an ECU 80 and memory 82 for, among other things, detecting the onset of an adverse event according to feedback from the electrodes 16, 52, 54. In an embodiment, the ECU 80 may be configured to execute instructions stored in the memory 82 to perform the functionality described herein such as, for example, detecting the onset of an adverse event based on feedback from the catheter 18. Such instructions may embody all or part of the method described in conjunction with FIG. 7 and/or similar methods and algorithms. For example, the ECU 80 may be configured to receive a signal based on the biological activity of a patient and detected from inside the patient such as, for example, an electrogram as described above. Biological activity, as used herein, may include, but is not limited to, electrical or other natural activity of an organ, such as the heart, kidneys, or lungs. The ECU 80 may be further configured to analyze the signal to yield a data set, such as, for example, one or more values indicative of the amount of noise present on an electrogram. The ECU 80 may be further configured to compare the data set to a threshold parameter (which may be stored in the memory 82), and to modify the provision of ablation energy from the signal generator 60 according to the comparison—i.e., one of the preemptive actions noted above. For example, if the amount of noise in an electrogram signal is indicative of an oncoming adverse event, the ECU 80 may cause the ablation generator 26 to reduce the amount of ablation energy provided, or to cease the provision of energy entirely. The ablation generator 26 may also include an output mechanism to output an indication for the physician/clinician that an adverse event is imminent so that the physician/clinician can retract the catheter, if desired. The output mechanism can include visual, audible, tactile, or other forms of output. In an embodiment, the EP monitor 30 may act as or contain such an output mechanism, and the ablation controller 26 may be configured to output a signal to the EP monitor 30 to provide an indication of an imminent adverse event.

The ECU 80 may comprise a programmable microprocessor or microcontroller, or may comprise an application specific integrated circuit (ASIC). The ECU 80 may include a central processing unit (CPU) and an input/output (I/O) interface through which the ECU 80 may receive a plurality of input signals including, for example, signals generated by electrodes 16, 52, 54, and generate a plurality of output signals including, for example, those used to control the amount of ablation energy provided by the ablation generator 26. The ECU 80 may be configured to perform various functions, such as those described in greater detail above and below, with appropriate programming instructions or code embodied in software, hardware, and/or other medium.

The tissue sensing circuit 28 provides a means, such as a tissue sensing signal source 62, for generating an excitation signal used in impedance measurements and means, such as a complex impedance sensor 64, for resolving the detected impedance into its component parts. In another exemplary embodiment, the complex impedance may be measured using components other than the tissue sensing circuit 28, such as, for example, the ablation generator 26. However, in an embodiment wherein the tissue sensing circuit is used, the signal source 62 is configured to generate an excitation signal across source connectors SOURCE (+) and SOURCE (−) (See FIG. 2). In some embodiments, the source 62 may output a signal having a frequency within a range from about 1 kHz to over 500 kHz, more preferably within a range of about 2 kHz to 200 kHz, and even more preferably about 20 kHz. In one embodiment, the excitation signal is a constant current signal, preferably in the range of between about 20-200 µA, and more preferably about 100 µA. As discussed below, the constant current AC excitation signal generated by the source 62 is configured to develop a corresponding AC response voltage signal that is dependent on the complex impedance of the tissue 12 and is sensed by the complex impedance sensor 64. The sensor 64 resolves the complex impedance into its component parts (i.e., the resistance (R) and reactance (X) or the impedance magnitude (|Z|) and phase angle (∠Z or ϕ)). Sensor 64 may include conventional filters (e.g., bandpass filters) to block frequencies that are not of interest, but permit appropriate frequencies, such as the excitation frequency, to pass. Signal processing software can be used to obtain the component parts of the measured complex impedance.

The circuit 28 is also connected, for a purpose described hereinbelow, across a pair of sense connectors: a positive polarity connector SENSE (+) which may connect to the tip electrode 16; and a negative polarity connector SENSE (−) which may be electrically connected to one of the patch electrodes 20, 22, 24 (see FIG. 2) As discussed further below, the connector SENSE (−) should be connected to a different electrode of the electrodes 20, 22, 24 relative to the connector SOURCE (−). It should again be understood that the term connectors as used herein does not imply a particular type of physical interface mechanism, but is rather broadly contemplated to represent one or more electrical nodes.

Figure 2:
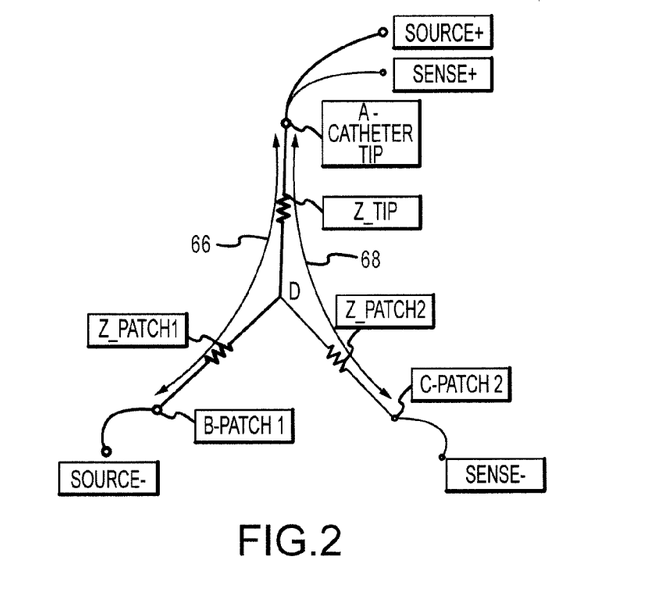
FIG. 2 is a simplified schematic diagram illustrating how a biological impedance may be determined.

Referring now to FIG. 2, connectors SOURCE (+), SOURCE (−), SENSE (+) and SENSE (−) form a three terminal arrangement permitting measurement of the complex impedance at the interface of the tip electrode 16 and the tissue 12. Complex impedance can be expressed in rectangular coordinates as set forth in equation (1):

$$Z = R + jX \quad (1)$$

where R is the resistance component (expressed in ohms); and X is a reactance component (also expressed in ohms). Complex impedance can also be expressed in polar coordinates as set forth in equation (2):

$$Z = r \cdot e^{j\theta} = |Z| \cdot e^{j\angle Z} \quad (2)$$

where |Z| is the magnitude of the complex impedance (expressed in ohms) and ∠Z=θ is the phase angle expressed in radians. Alternatively, the phase angle may be expressed in terms of degrees where $$\phi = \left(\frac{180}{\pi}\right)\theta.$$

Throughout the remainder of this specification, phase angle will be referenced in terms of degrees. The three terminals comprise: (1) a first terminal designated "A-Catheter Tip" which is the tip electrode 16; (2) a second terminal designated "B-Patch 1" such as the source return patch electrode 24; and (3) a third terminal designated "C-Patch 2" such as the sense return patch electrode 22. In addition to the ablation (power) signal generated by the source 60 of the ablation generator 26, the excitation signal generated by the source 62 in the tissue sensing circuit 28 is also applied across the source connectors (SOURCE (+), SOURCE (−)) for the purpose of inducing a response signal with respect to the load that can be measured and which depends on the complex impedance.

As described above, in one embodiment, a 20 kHz, 100 µA AC constant current signal is sourced along a path 66, as illustrated, from one connector (SOURCE (+), starting at node A) through the common node (node D) to a return patch electrode (SOURCE (−), node B). The complex impedance sensor 64 is coupled to the sense connectors (SENSE (+), SENSE (−)), and is configured to determine the impedance across a path 68. For the constant current excitation signal of a linear circuit, the impedance will be proportional to the observed voltage developed across SENSE (+)/SENSE (−), in accordance with Ohm's Law: Z=V/I. Because voltage sensing is nearly ideal, the current flows through the path 66 only, so the current through the path 68 (node D to node C) due to the excitation signal is effectively zero. Accordingly, when measuring the voltage along the path 68, the only voltage observed will be where the two paths intersect (i.e., from node A to node D). Depending on the degree of separation of the two patch electrodes (i.e., those forming nodes B and C), an increasing focus will be placed on the tissue volume nearest the tip electrode 16. If the patch electrodes are physically close to each other, the circuit pathways between the catheter tip electrode 16 and the patch electrodes will overlap significantly and impedance measured at the common node (i.e., node D) will reflect impedances not only at the interface of the catheter electrode 16 and the tissue 12, but also other impedances between the tissue 12 and the surface of body 14. As the patch electrodes are moved further apart, the amount of overlap in the circuit paths decreases and impedance measured at the common node is only at or near the tip electrode 16 of the catheter 18.

Figure 3:
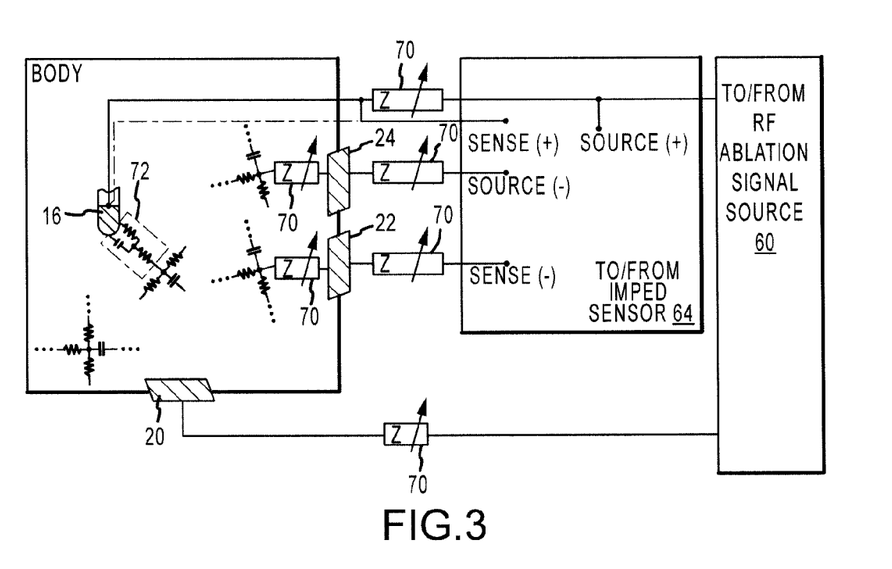
FIG. 3 is a schematic and block diagram illustrating the approach for determining a biological impedance in FIG. 2 in greater detail.

Referring now to FIG. 3, the concept illustrated in FIG. 2 is extended. FIG. 3 is a simplified schematic and block diagram of a three-terminal measurement arrangement. For clarity, it should be pointed out that the SOURCE (+) and SENSE (+) lines may be joined in the catheter connector 42 or the handle 44 (as in solid line) or may remain separate all the way to the tip electrode 16 (the SENSE (+) line being shown in phantom line from the handle 44 to the tip electrode 16). FIG. 3 shows, in particular, several sources of complex impedance variations, shown generally as blocks 70, which are considered "noise" because such variations do not reflect the physiologic changes in the tissue 12 whose complex impedance is being measured. For reference, the tissue 12 whose complex impedance is being measured is that near and around the tip electrode 16 and is enclosed generally by a phantom-line box 72 (and the tissue 12 is shown schematically, in simplified form, as a resistor/capacitor combination). One object is to provide a measurement arrangement that is robust or immune to variations that are not due to changes in or around the box 72. For example, the variable complex impedance boxes 70 that are shown in series with the various cable connections (e.g., in the SOURCE (+) connection, in the SOURCE (−) and SENSE (−) connections, etc.) may involve resistive/inductive variations due to cable length changes, cable coiling, and the like. The variable complex impedance boxes 70 that are near the patch electrodes 22, 24, may be more resistive/capacitive in nature, and may be due to body perspiration and the like over the course of a study. The arrangement may be relatively immune to the variations in the blocks 70, exhibiting a high signal-to-noise (S/N) ratio as to the complex impedance measurement for the block 72.

Although the SOURCE (−) and SENSE (−) returns are illustrated in FIG. 3 as patch electrodes 22, 24, it should be understood that other configurations are possible. For example, the indifferent/dispersive return electrode 20 can be used as a return as well as another electrode 52, 54 on the catheter 18 as described in U.S. patent application Ser. No. 11/966,232, which is hereby incorporated by reference in its entirety as though fully set forth herein.

Although a number of methods for assessing adverse events according to an impedance monitored as described in accordance with FIGS. 1 through 3 are described in detail in U.S. Patent Application Publication No. 2011/0144657, incorporated above, a brief description of one of the number of methods follows.

In an exemplary embodiment, the ECU 34 may be further configured to acquire one or more values for one or more components of a complex impedance between the electrode 16 and the tissue 12 (i.e., the resistance (R) and reactance (X), or the impedance magnitude (|Z|) and phase angle (φ), or any combination of the foregoing or derivatives or functional equivalents thereof). The ECU 34 may acquire these values by receiving them from the complex impedance sensor 64, or by obtaining them from a memory or storage medium associated with, or accessible by, the ECU 34. In an exemplary embodiment, the ECU 34 may be configured to calculate an index responsive to at least the value(s) of the one or more components of the complex impedance, with the index indicative of a likelihood of an adverse event such as, for example, barotrauma (i.e., endocardial barotrauma) occurring in the tissue 12. In another exemplary embodiment, the ECU 34 may be further configured to acquire one or more values for the power or energy applied to the tissue 12 by the ablation generator 26 during the formation of a lesion in the tissue 12. In such an embodiment, the ECU 34 is configured to calculate the index responsive to the value(s) of the one or more components of the complex impedance and the value(s) of the applied power. The ECU 34 may be further configured to assess the stability of the catheter 18, and therefore, the electrodes 16, 52, 54 mounted thereon.

Additionally, in an embodiment of the system 10 such as that briefly described above wherein multiple excitation signals are utilized to determine multiple complex impedances, the ECU 34 may be configured to acquire one or more values of components of one or more complex impedances for calculating the index. For the sake of clarity and brevity, the following description will be limited to the calculation of the index using a single complex impedance. It should be understood, however, that the present disclosure is not meant to be limited to such an embodiment, but rather includes embodiments wherein components of multiple complex impedances are used in the calculation of the index.

The ECU 34 is configured to predict the likelihood of endocardial barotrauma occurring in tissue during lesion formation therein (e.g., using an equation that calculates an index that is indicative of the likelihood of barotrauma occurring in the tissue). Factors that may be involved in prediction by the ECU 34 include, for example, resistance (R), reactance (X), magnitude of impedance (Z), electrical coupling index (ECI), and phase angle (φ) prior to the onset of lesion formation in the tissue. The R, X, Z, ECI, and φ at the start of lesion formation may also be involved. In addition, the magnitude of change in, or slope of, R, X, Z, ECI, and φ from the start of lesion formation, or at some point in time after the start of lesion formation, to the end of lesion formation or to a point in time subsequent to the start of lesion formation and prior to the end of lesion formation, as well as the maximum rate of change for R, X, Z, ECI, and φ from the start of lesion formation to the end of lesion formation may be involved. Further, the mean RF power applied to the tissue during lesion formation, the RF duration, the natural log of the RF duration, the product of the RF power and the RF duration, and the electrical current used may also be involved.

In one exemplary embodiment, the resistance (R) and reactance (X) components of the complex impedance between the electrode 16 and the tissue 12, and the power applied to the tissue 12 may be considered in an algorithm applied by the ECU 34. More specifically, the changes in resistance (dR) and reactance (dX) from the start of the formation of a lesion to a subsequent point in time in the formation process of the same lesion, the change in resistance (dR) divided by the change in time (dt) from the start of the lesion formation process to the point in time the index is being calculated (dR/dt), and an electrical current value calculated by taking the square root of the quotient of the division of the mean value of the RF power applied to the tissue 12 from the start of the lesion formation process to the point in time the index is being calculated by the value of the resistance ($R_0$) between the electrode 16 and the tissue 12 just prior to the start or onset of the lesion formation process (i.e., $$\left(i.e., \sqrt{\frac{MeanPower}{R_0}}\right)$$

may be considered in such an algorithm.

Several factors can potentially have an impact on the accuracy of the prediction algorithm. Such factors can include, for example and without limitation, certain parameters and/or characteristics of the equipment and/or arrangement of the system 10 (such as, for example, the type of catheter and ablation generator being used, the irrigation flow rate, etc.) Accordingly, in an embodiment, a computationally efficient index may be based on the "electrical" factors above (i.e., resistance, reactance, power values, etc.), as well as certain predetermined coefficients and constants to account for design parameters or characteristics of the devices/equipment used in the ablation procedure. Such an index may be determined, for example, according to equation (3) below:

$$\text{Index} = a + b_1 * \frac{dR}{dt} + b_2 * I + b_3 * dR + b_4 * dX \quad (3)$$

In equation (3), the constant a and the coefficients $b_1$-$b_4$ are predetermined values that are intended to account for the various factors associated with, for example, the equipment used in the ablation procedure (i.e., type of catheter and/or ablation generator, irrigation flow rate, etc.). The constant and coefficients can be determined in a number of ways, such as, for example, controlled experimentation or using analyses, such as, for example, a regression analysis. Once the constant and coefficients are determined, they may be stored or programmed into the ECU 34, or a memory/storage device 80 (see FIG. 1) associated therewith or accessible thereby. Alternatively, the catheter 18 may itself include a memory such as an EEPROM that stores numerical values for the coefficients and constant corresponding to that particular type of catheter and/or other equipment of the system 10, or stores a memory address for accessing the numerical values in another memory location. The ECU 34 may retrieve these values or addresses directly or indirectly and factor them into the index calculation accordingly.

Referring again to FIG. 1, the EP monitor 30 is configured to display electrophysiology data including, for example, an electrogram. The EP monitor 30 may display an electrogram obtained from patches (not shown) placed on the exterior of the body, or from an internal source, such as the ablation catheter 18. The monitor 30 can be conventional in the art and may comprise an LCD or CRT monitor or another conventional monitor. The monitor 30 may receive inputs from the ablation generator 26 as well as other conventional EP lab components not shown in the illustrated embodiment. In an embodiment, the EP monitor 30 may be configured to output one or more indications of an adverse event. An indication may be visual, audible, or of another form known in the art.

The mapping and navigation system 32 is provided for visualization, mapping, and/or navigation of the ablation catheter 18 and/or internal body structures and may be referred to herein as "the navigation system." In some embodiments, the navigation system 32 comprises an electric field-based system, such as, for example, the ENSITE VELOCITY cardiac electro-anatomic mapping system available from St. Jude Medical, Inc., of St. Paul, Minn. and described, for example, in U.S. Pat. No. 7,263,397, which is hereby incorporated by reference in its entirety as though fully set forth herein. In other exemplary embodiments, the navigation system 32 may comprise systems other than electric field-based systems. For example, the navigation system 32 may comprise a magnetic field-based system such as the CARTO system commercially available from Biosense Webster, and as generally described in U.S. Pat. Nos. 6,498,944; 6,788,967; and 6,690,963, the disclosures of which are hereby incorporated by reference in their entireties as though fully set forth herein. In another exemplary embodiment, the navigation system 32 may comprise a magnetic field-based system based on the MEDIGUIDE technology available from St. Jude Medical, Inc. and described, for example, in U.S. Pat. Nos. 6,233,476; 7,197,354; and 7,386,339, which are hereby incorporated by reference in their entireties as though fully set forth herein. In yet another embodiment, the navigation system 32, may comprise a combination electric field-based and magnetic field-based system, such as, for example and without limitation, the system described in pending U.S. patent application Ser. No. 13/231,284, the disclosure of which is hereby incorporated by reference in its entirety as though set fully forth herein, or the CARTO 3 system commercially available from Biosense Webster. In yet still other exemplary embodiments, the navigation system 32 may comprise or be used in conjunction with other commonly available systems, such as, for example and without limitation, fluoroscopic, computed tomography (CT), and magnetic resonance imaging (MRI)-based systems. For purposes of illustration only, the navigation system 32 will be described with reference to an embodiment in which the navigation system 32 is an electrical field-based system.

Figure 4:
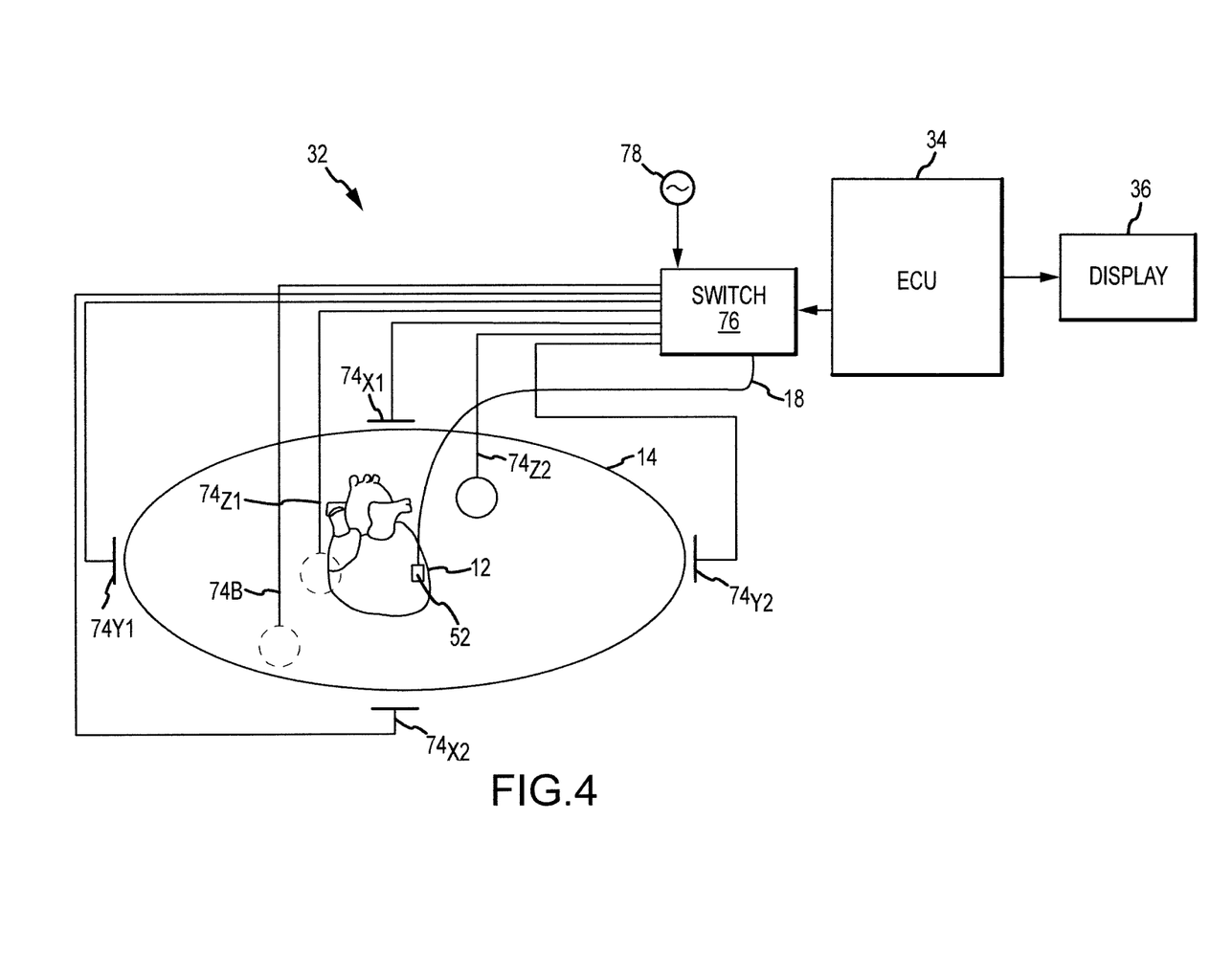
FIG. 4 is a simplified schematic diagram illustrating an example navigation system for use with the system of FIG. 1.

With reference to FIGS. 1 and 4, the system 32 may include a plurality of patch electrodes 74, the ECU 34, and the display device 36, among other components. However, as briefly described above, in another exemplary embodiment, the ECU 34 and/or the display device 36 may be separate and distinct components that are electrically connected to, and configured for communication with, the system 32.

With the exception of the patch electrode $74_B$ (often referred to as a "belly patch"), the patch electrodes 74 are provided to generate electrical signals used, for example, in determining the position and orientation of the catheter 18 and in the guidance thereof. In one embodiment, the patch electrodes 74 are placed orthogonally on the surface of the body 14 and are used to create axes-specific electric fields within the body 14. For instance, in one exemplary embodiment, patch electrodes $74_{X1}$, $74_{X2}$ may be placed along a first (x) axis. Patch electrodes $74_{Y1}$, $74_{Y2}$ may be placed along a second (y) axis, and patch electrodes $74_{Z1}$, $74_{Z2}$ may be placed along a third (z) axis. Each of the patch electrodes 74 may be coupled to a multiplex switch 76. In an exemplary embodiment, the ECU 34 is configured, through appropriate software, to provide control signals to switch 76 to thereby sequentially couple pairs of electrodes 74 to a signal generator 78. Excitation of each pair of electrodes 74 generates an electrical field within body 14 and within an area of interest such as tissue 12. Voltage levels at non-excited electrodes 74, which are referenced to the belly patch $74_B$, are filtered and converted and provided to ECU 34 for use as reference values.

As briefly discussed above, the catheter 18 includes one or more electrodes mounted therein or thereon (i.e., electrodes 16, 52, 54). In an exemplary embodiment, at least one of the electrodes comprises a positioning electrode and is configured to be electrically coupled to the ECU 34. In an exemplary embodiment, the electrode 52 comprises a positioning electrode (positioning electrode 52). With the positioning electrode 52 electrically coupled to the ECU 34, the positioning electrode 52 is placed within electrical fields created in the body 14 (e.g., within the heart) by exciting the patch electrodes 74. The positioning electrode 52 experiences voltages that are dependent on the location between the patch electrodes 74 and the position of the positioning electrode 52 relative to tissue 12. Voltage measurement comparisons made between the electrode 52 and the patch electrodes 74 can be used to determine the position of the positioning electrode 52 relative to the tissue 12. Movement of the positioning electrode 52 proximate the tissue 12 (e.g., within a heart chamber) produces information regarding the geometry of the tissue 12. This information may be used, for example, to generate models and maps of anatomical structures. Information received from the positioning electrode 52 can also be used to display on a display device, such as display device 36, the location and orientation of the positioning electrode 52 and/or the tip of the catheter 18 relative to the tissue 12. Accordingly, among other things, the ECU 34 of the system 32 provides a means for generating display signals used to the control display device 36 and the creation of a graphical user interface (GUI) on the display device 36.

In addition to the above, the ECU 34 may further provide a means for controlling various components of system 28 including, but not limited to, the multiplex switch 76. It should be noted that while in an exemplary embodiment the ECU 34 is configured to perform some or all of the functionality described above and below, in another exemplary embodiment, the ECU 34 may be separate and distinct from the system 32, and the system 32 may have another processor (e.g., another ECU) configured to perform some or all of the functionality described herein. In such an embodiment, the processor of the system 32 would be electrically coupled to, and configured for communication with, the ECU 34. However, for purposes of clarity and illustration only, the description below will be limited to an embodiment wherein ECU 34 is part of system 32 and is configured to perform the functionality described herein.

The ECU 34 may comprise a programmable microprocessor or microcontroller, or may comprise an application specific integrated circuit (ASIC). The ECU 34 may include a central processing unit (CPU) and an input/output (I/O) interface through which the ECU 34 may receive a plurality of input signals including, for example, signals generated by patch electrodes 74 and the positioning electrode 52 (among others), and generate a plurality of output signals including, for example, those used to control the display device 36 and the switch 76. The ECU 34 may be configured to perform various functions, such as those described in greater detail above and below, with appropriate programming instructions or code (e.g., embodied in software, hardware, and/or other medium). Accordingly, the ECU 34 may be programmed with one or more computer programs encoded on a computer-readable storage medium for performing the functionality described herein.

In operation, the ECU 34 generates signals to control the switch 76 to thereby selectively energize the patch electrodes 74. The ECU 34 receives position signals (location information) from the catheter 18 (and particularly the positioning electrode 52) reflecting changes in voltage levels on the positioning electrode 52 and from the non-energized patch electrodes 74. The ECU 34 uses the raw positioning data produced by the patch electrodes 74 and positioning electrode 52 and corrects the data to account for respiration, cardiac activity, and other artifacts using known or hereafter developed techniques. The corrected data may then be used by the ECU 34 in a number of ways, such as, for example and without limitation, to create a model of an anatomical structure, to map electrophysiological data on an image or model of the tissue 12 generated or acquired by the ECU 34, or to create a representation of the catheter 16 that may be superimposed on a map, model, or image of the tissue 12 generated or acquired by the ECU 34.

Figure 5:
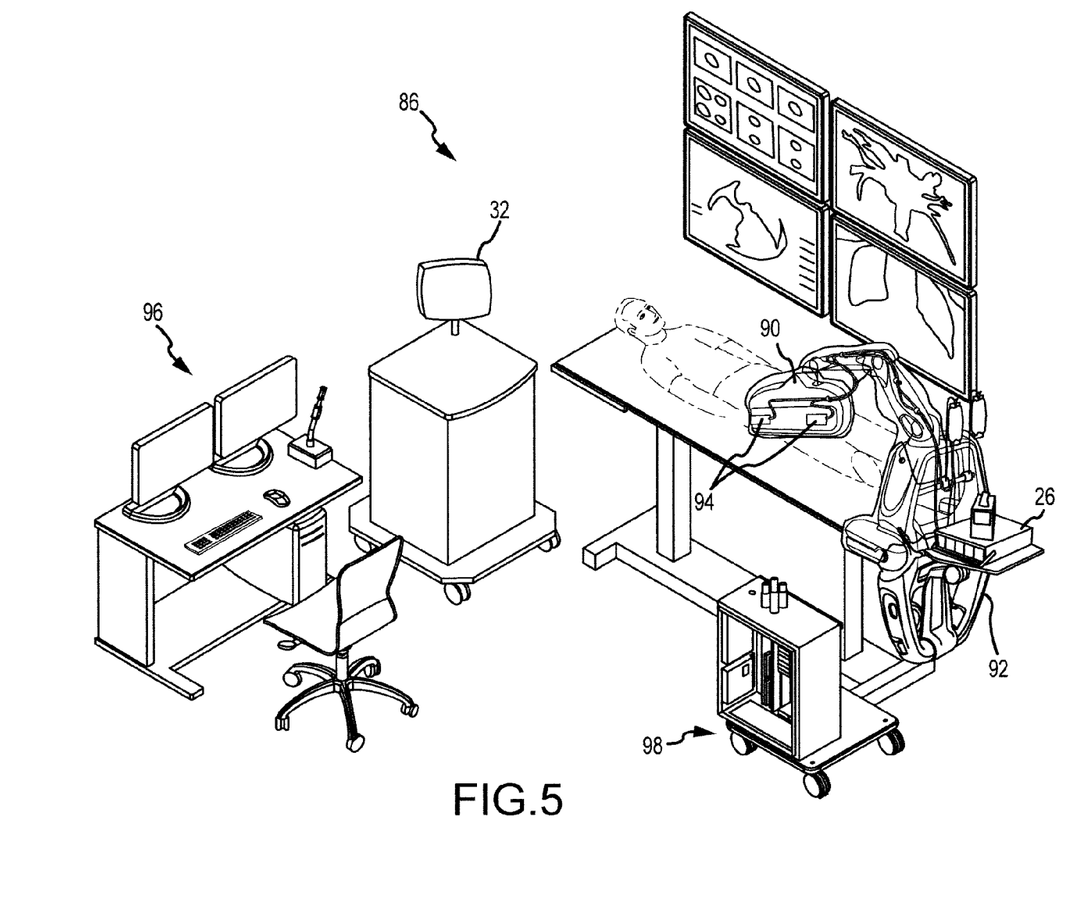
FIG. 5 is an isometric diagrammatic view of a robotic catheter system illustrating an exemplary layout of various system components.
Figure 6:
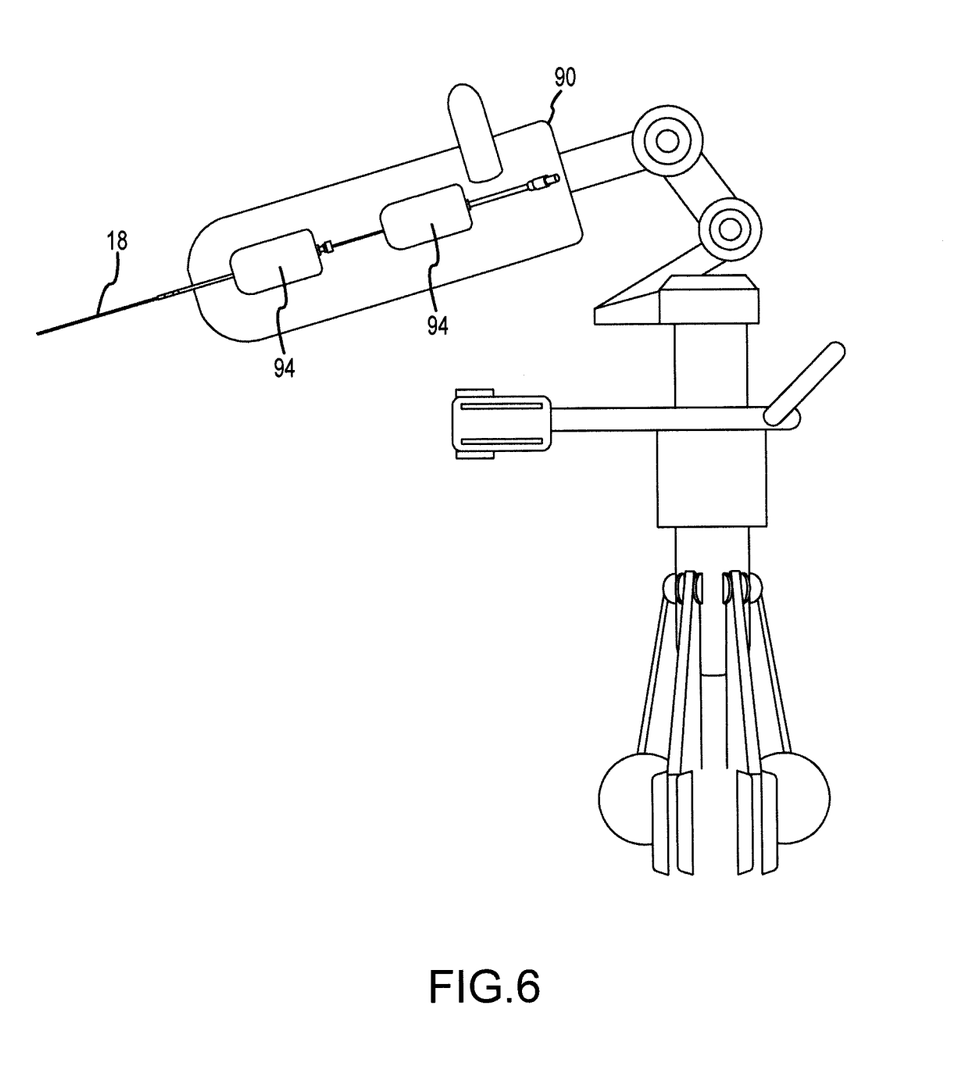
FIG. 6 is an isometric diagrammatic view of an exemplary embodiment of a robotic catheter manipulator support structure.

As noted above, in an embodiment, the catheter 18 may be controlled by a remote catheter guidance system (RCGS), such as a robotic catheter system. With reference to FIGS. 5 and 6, an RCGS 86 will be briefly described. A more detailed description of the RCGS 86 is set forth in U.S. Patent Application Publication No. 2009/0247993, the disclosure of which is hereby incorporated by reference in its entirety as though fully set forth herein.

The RCGS 86 provides the ability for precise and dynamic automated control in, for example, diagnostic, therapeutic, mapping, and ablative procedures. In an exemplary embodiment, and as shown in FIGS. 5 and 6, the RCGS 86 includes one or more robotic catheter manipulator assemblies 90 supported on a manipulator support structure 92. In some embodiments, the manipulator support structure 92 further includes the ablation generator 26. The robotic catheter manipulator assembly 90 may include one or more removably mounted robotic catheter device cartridges 94, for example, that are generally linearly movable relative to the robotic catheter manipulator assembly 90 to cause a medical device associated therewith (e.g., catheter 18) to be moved (e.g., advanced, retracted, etc.). The catheter manipulator assembly 90 serves as the mechanical control for the movements or actions of the cartridge 94. The RCGS 86 may further include a human input device and control system ("input control system") 96, which in some embodiments includes a joystick and related controls with which a physician/clinician may interact to control the manipulation of the cartridge 94, and therefore, the catheter 18 of the RCGS 86. The robotic catheter system 86 may still further include an electronic control system 98, which, in an exemplary embodiment, includes a controller which translates motions of the physician/clinician at the input device into resulting movements of the catheter 18. As with the system 10 described above, the RCGS 86 may further include the visualization, mapping and/or navigation system 32, to provide the clinician/physician with real-time or near-real-time positioning information concerning the catheter and various types of anatomical maps, models, and/or geometries of the cardiac structure of interest, for example.

In addition to, or lieu of, the manual control provided by the input control system 96, the RCGS 86 can also be configured to provide automated catheter movement. For example, in one exemplary embodiment, a physician/clinician may identify locations that potentially form a path) on a rendered computer model of the cardiac structure. The RCGS 86 can be configured to relate those digitally selected points to actual positions within the patient's anatomy, and may command and control the movement of the catheter 18 to defined positions. Once in a defined position, either the physician/clinician or the RCGS 86 could be used perform desired treatment or therapy, perform diagnostic evaluations, or perform some other function. The RCGS 86 could enable full robotic control by using optimized path planning routines together with the visualization, mapping, and/or navigation system 32.

In some embodiments, an electrogram, such as an intracardiac electrogram, can be used to detect an imminent adverse event. Such an electrogram, or command signals based on such an electrogram (e.g., produced by the ablation generator 26), may be input into the electronic control system 98 and may be used in the control and operation of the RCGS 86. In an exemplary embodiment, the electrogram may be generated by, for example, one or more electrodes on the catheter 18, as described in detail above. The electrogram may be monitored by the ablation generator 26, in some embodiments. If a monitored electrogram indicates that an adverse event is imminent, the ablation generator 26 may reduce the ablation energy provided. Additionally or alternatively, the ablation generator 26 may generate a signal for the controller 80 to retract the ablation catheter 18 from the ablation site.

In an embodiment, the electronic control system 98 can be configured to receive and monitor an electrogram for indications of an adverse event, substantially as described above and below. The electronic control system 98 can thus be configured to control the ablation energy provided by the ablation generator 26. In response to an electrogram indication that an adverse event is imminent, the electronic control system 98 may reduce the ablation energy provided by the ablation generator 26, instruct the manipulator assembly 90 to retract the catheter 18, and/or take some other preemptive action to attempt to prevent the adverse event. The electronic control system 98 may be configured to execute instructions to assess the electrogram and perform such preemptive action, as described above and below.

Figure 7:
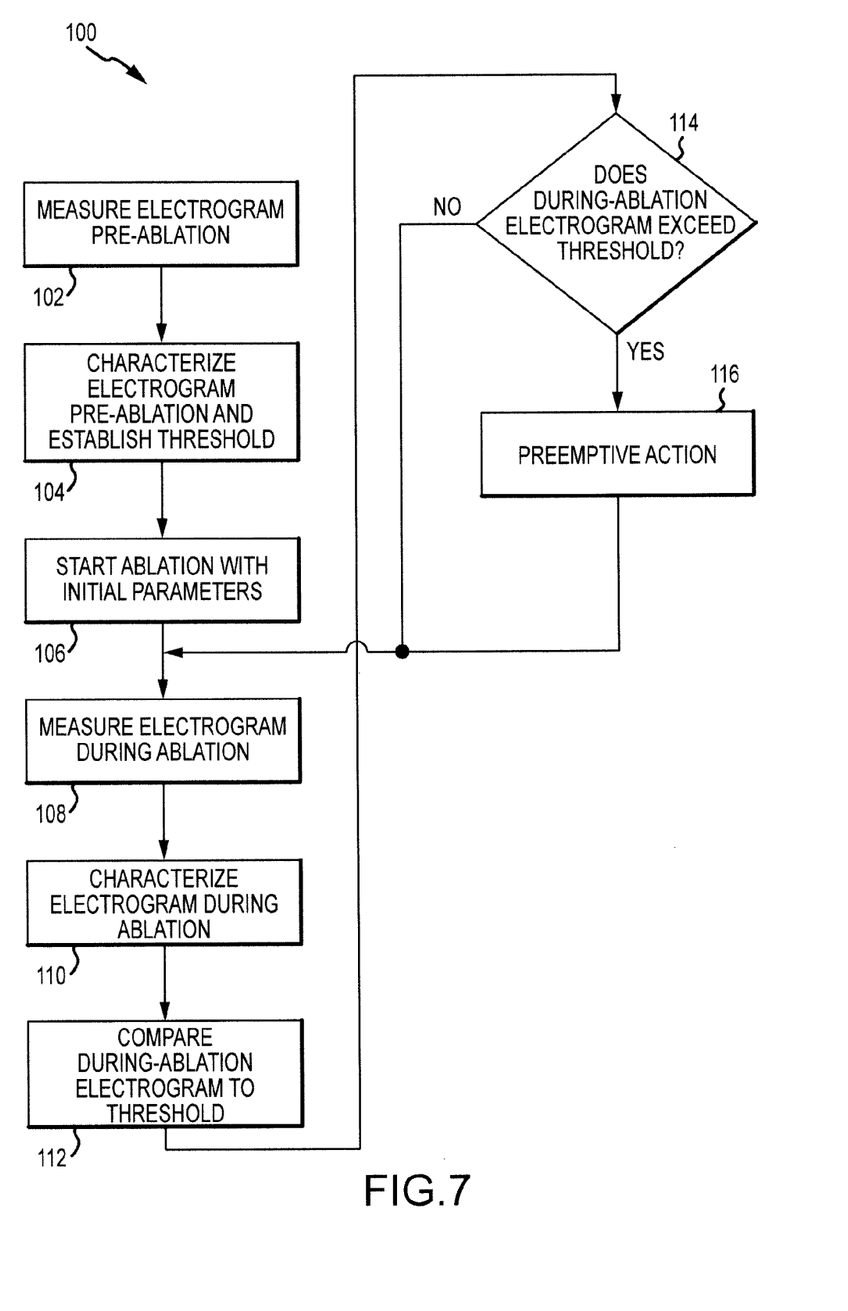
FIG. 7 is a flow chart illustrating an exemplary method of controlling the provision of ablation energy during an ablation procedure.

FIG. 7 is a flow chart illustrating an exemplary method 100 of controlling the provision of ablation energy during an ablation procedure. In some embodiments, for example, the method may comprise a method for controlling the provision of ablation energy based on the detection of one or more adverse events using an electrogram. As noted above, the method 100 can be executed by, for example and without limitation, an ablation generator 26, an RCGS electronic control system 98, or some other system, device, or apparatus. Accordingly, the method 100 can be embodied in instructions (i.e., code) stored in memory to be executed by an electronic control unit.

The method 100 can begin with a step 102 of measuring or sensing an electrogram before an ablation procedure—i.e., before the application of ablation energy to a target site. The electrogram measured can be a unipolar electrogram, a multi-polar electrogram, or some other type of electrogram known in the art. In an embodiment, the electrogram can be measured from inside a tissue of interest such as, for example, a heart or a chamber of the heart. In an embodiment, both an intracardiac unipolar electrogram and an intracardiac multi-polar electrogram can be measured pre-ablation.

The method 100 further includes a step 104 of characterizing the pre-ablation electrogram. The pre-ablation characterizing step can include assessing the pre-ablation electrogram to establish the "normal" characteristics of the electrogram such as, for example and without limitation, the frequency content of the electrogram and/or the amplitudes of the electrogram at selected frequencies. In an embodiment, the pre-ablation characterization step can comprise a frequency domain analysis (e.g., power spectrum, spectral shift), a time domain analysis (e.g., moving average, auto-correlation, cross-correlation), and/or a multi-dimensional analysis (e.g., wavelet). The analysis can also include the use of one or more algorithms known in the art such as, for example, a Fast Fourier Transform (FFT). The result of the characterization step may be, in embodiments, a data set including one or more items of data. The items of data may include, for example and without limitation, signal frequencies and signal amplitudes.

The pre-ablation characterizing step 104 can also include establishing one or more thresholds based on one or more of the analyses described above. For example, the threshold may be a certain amplitude at a particular frequency, a certain frequency spectrum, and the like. A threshold may be selected such that any signal content that exceeds the threshold can be considered noise—i.e., abnormal and/or unexpected electrogram activity. Accordingly, the threshold may be selected according to a characterization of the subject patient's electrogram. Of course, more than one threshold may be selected, either for a single analysis type, or for multiple analysis types.

It should be understood that a "threshold" may include one or more values or a range of values with an upper and lower boundary. As understood herein, a particular value may "exceed" a particular threshold by being either above or below a particular value or range of values.

The pre-ablation characterization and threshold establishment can be dynamic, i.e., based on data collected during a patient's particular procedure. Dynamic pre-ablation characterization may be used to account for factors unique to a particular patient or procedure such as, for example, any noise caused by equipment in the operating environment (e.g., a fluid pump, an ablation generator), as well as the particular electrical activity of the patient's heart.

Once the electrogram has been characterized and one or more thresholds established, the method 100 can continue to a step 106 of starting ablation with initial ablation parameters. Such parameters can include, for example, an initial frequency, current, voltage, and power.

During the application of ablation energy, the method 100 can include a number of steps 108, 110, 112, 114, 116 for detecting and attempting to avert an adverse event. One or more of the in-ablation steps 108, 110, 112, 114, 116 may be performed on an ongoing basis during an ablation procedure, as described below.

A step 108 of sensing an electrogram during ablation can be performed in a similar fashion as the pre-ablation electrogram measurement in step 102. That is, the electrogram measured can be a unipolar electrogram, a multi-polar electrogram, or some other type of electrogram known in the art. In an embodiment, the electrogram can be sensed from inside a tissue of interest such as, for example, a heart or a chamber of the heart. In an embodiment, both an intracardiac unipolar electrogram and an intracardiac multi-polar electrogram can be sensed during ablation for comparison to unipolar and multi-polar intracardiac electrograms measured pre-ablation.

The in-ablation electrogram can then be characterized in step 110 in a similar fashion to how the pre-ablation electrogram was characterized. That is, one or more analysis methods or algorithms may be applied to the electrogram, such as a frequency-domain, time-domain, and/or multi-dimensional analysis. In an embodiment, an FFT may be applied to the in-ablation electrogram. The analytical method or methods applied to the in-ablation electrogram for characterizing the in-ablation electrogram may be the same as the analytical method or methods applied to the pre-ablation electrogram. Alternatively, and in other embodiments, a different analytical method or methods may be employed for characterizing the in-ablation electrogram.

The method 100 further comprises a step 112 of comparing the during-ablation electrogram to the threshold established in the pre-ablation electrogram characterization step, and a step 114 of querying whether the during-ablation electrogram exceeds that threshold. In some embodiments, the comparison and query steps 112, 114 can be performed substantially simultaneously and can be performed to determine whether the during-ablation electrogram has exceeded the threshold, such that the level of noise in the during-ablation electrogram indicates that an adverse event is imminent.

If the during-ablation electrogram exceeds an established threshold (i.e., the answer to the query step 114 is affirmative), the method 100 further comprises the step 116 of taking preemptive action to prevent the adverse event suggested by the noise in the electrogram from occurring. In some embodiments, the preemptive action can include altering the ablation parameters by, for example and without limitation, reducing or ceasing the provision of ablation energy to the ablation site. The preemptive action may also include retracting the ablation catheter from the ablation site, either manually or via RCGS, and/or increasing or otherwise altering the flow of irrigation fluid. In an embodiment, the preemptive action can include outputting an indication of an imminent adverse event to notify a physician/clinician that the ablation catheter should be manually retracted from the ablation site. Once preemptive action is taken, the method can return to the step of measuring an electrogram during ablation.

If the during-ablation electrogram does not exceed an established threshold (i.e., if the answer to the query step 114 is negative), the method can return to the step 108 of measuring an electrogram during ablation. Of course, as noted above, the in-ablation steps 108, 110, 112, 114, 116 may be continuously performed during an ablation procedure to monitor an electrogram in real time and attempt to avert any adverse event or events suggested by the electrogram.

Figure 8:
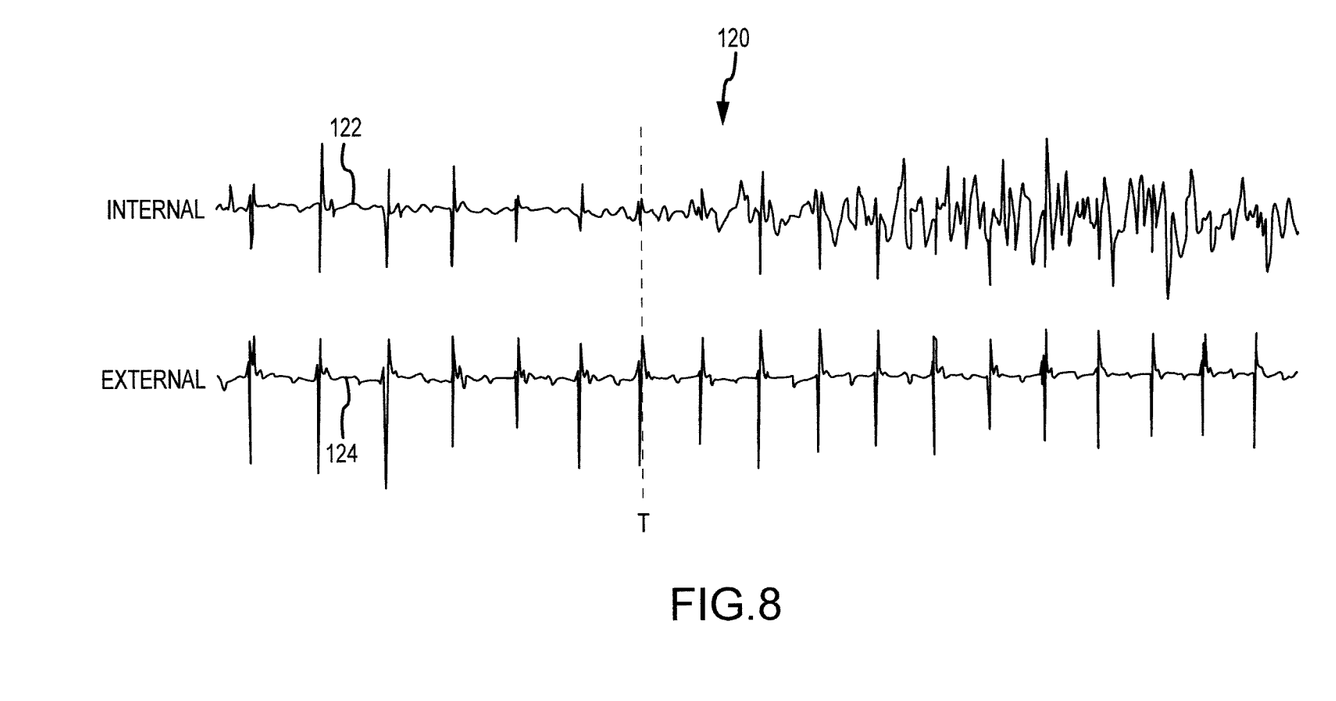
FIG. 8 is a plot illustrating an exemplary intracardiac electrogram and an external electrogram generated using the system of FIG. 1.

FIG. 8 is a plot 120 illustrating an exemplary intracardiac electrogram 122 and an exemplary external electrogram 124. In the illustrated embodiment, the entire electrogram signal is acquired during the provision of ablation energy to an anatomical site. Early portions of both the intracardiac electrogram 122 and the external electrogram 124 indicate normal heart activity. At time point T, however, the characteristics of the intracardiac electrogram 122 change—i.e., an increasing amount of noise appears on the signal—and continues through a later portion of the electrogram 122. In contrast, the external electrogram 124 continues to show normal electrical activity of the heart. The onset of noise at time T may indicate the onset of an adverse event. According to the systems and methods described herein, preemptive action could be taken at or around time T to prevent the adverse event suggested by the noise present in the intracardiac electrogram 122.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A device for controlling the provision of ablation energy, the device comprising:
   a memory configured to store a threshold parameter indicative of previously-measured electrical activity of a tissue of a patient, wherein the threshold is determined from a characterization of an electrogram; and
   an electronic control unit (ECU) configured to:
      receive an electrogram respective of the patient detected from inside the patient;
      analyze said electrogram to yield a data set comprising frequency content of said electrogram;
      compare at least a portion of said data set to said threshold parameter to detect an adverse event; and
      modify the provision of ablation energy based, at least in part, on a comparison of said data set to said threshold parameter.

2. The device of claim 1, wherein said data set comprises one or more amplitudes of said electrogram at one or more frequencies.

3. The device of claim 2, wherein said threshold parameter comprises one or more amplitudes at one or more frequencies.

4. The device of claim 1, wherein said ECU is configured to analyze said electrogram using a time-series analysis.

5. The device of claim 1, wherein said ECU is configured to analyze said electrogram using a frequency-domain analysis.

6. The device of claim 1, wherein said ECU is configured to analyze said electrogram using a multi-dimensional analysis.

7. The device of claim 1, wherein said second electrogram comprises an intracardiac electrogram.

8. The device of claim 1, wherein said ECU is configured to modify the provision of ablation energy by interrupting the provision of ablation energy.

9. The device of claim 1, wherein said electrogram is a first electrogram and said data set is a first data set, further wherein said ECU is further configured to receive a second electrogram respective of the patient and detected from inside the patient, said second electrogram indicative of electrical activity of the tissue, analyze said second electrogram to yield a second data set comprising frequency content of the electrical activity, and establish said threshold parameter according to said second data set, further wherein said second electrogram is earlier in time than said first data set electrogram.

10. A system for performing an ablation procedure, the system comprising:
   an ablation generator configured to provide ablation energy to a medical device including one or more electrodes; and
   an electronic control unit (ECU) configured to:
      receive a signal detected with at least one of said one or more electrodes based on the biological activity of a patient and detected from inside the patient;
      analyze said signal to yield a data set comprising frequency content of said signal;
      compare at least a portion of said data set to a threshold parameter to detect an adverse event, said threshold parameter indicative of electrical activity of a tissue of the patient, wherein the threshold is determined from a characterization of an electrogram; and
      provide a command for said ablation generator to modify the provision of ablation energy based, at least in part, on a comparison of said data set to said threshold parameter.

11. The system of claim 10, wherein said signal comprises a unipolar electrogram detected using one of said one or more electrodes disposed on a distal tip of said medical device.

12. The system of claim 10, wherein said signal comprises a multi-polar electrogram detected using one of said one or more electrodes disposed on a distal tip of said medical device and at least another of said one or more electrodes.

13. The system of claim 10, further comprising an output mechanism configured to output an alert when said threshold parameter is exceeded.

14. A method for providing ablation energy, comprising:
   receiving a first electrogram respective of a patient and detected from within the patient;
   analyzing said first electrogram to yield a first data set comprising frequency content of said first electrogram;
   establishing a threshold parameter according to said first data set, wherein the threshold is determined from a characterization of the first electrogram;
   providing ablation energy for the ablation of a biological site;
   receiving a second electrogram respective of the patient and detected from within the patient after receiving said first electrogram;
   analyzing said second signal to yield a second data set comprising frequency content of said second electrogram;
   comparing at least a portion of said second data set to said threshold parameter to predict the likelihood of an adverse event; and
   modifying a parameter of provided ablation energy according to said comparison.

15. The method of claim 14, wherein said threshold parameter comprises an amplitude and a frequency.

16. The method of claim 14, wherein said analyzing steps comprise a time-series analysis.

17. The method of claim 14, wherein said analyzing steps comprise a frequency-domain analysis.

18. The method of claim 14, wherein said analyzing steps comprise a multi-dimensional analysis.

19. The method of claim 14, wherein said step of receiving said first electrogram is performed before said step of providing ablation energy.

20. The method of claim 19, wherein said step of receiving said second electrogram is performed substantially simultaneously with said step of providing ablation energy.

* * * * *